(12) United States Patent
Handrosch et al.

(10) Patent No.: US 8,114,211 B2
(45) Date of Patent: Feb. 14, 2012

(54) PEARLESCENT PIGMENTS

(75) Inventors: Carsten Handrosch, Muehital (DE);
Marcus Mathias, Gernsheim (DE);
Nicole Schupp, Gross-Bieberau (DE);
Meike Willius, Eich (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 129 days.

(21) Appl. No.: 12/520,151

(22) PCT Filed: Dec. 12, 2007

(86) PCT No.: PCT/EP2007/010869
§ 371 (c)(1),
(2), (4) Date: Jun. 19, 2009

(87) PCT Pub. No.: WO2008/077487
PCT Pub. Date: Jul. 3, 2008

(65) Prior Publication Data
US 2010/0021565 A1 Jan. 28, 2010

(30) Foreign Application Priority Data
Dec. 20, 2006 (DE) .......................... 10 2006 060 997

(51) Int. Cl.
*C09D 5/36* (2006.01)
*C09C 1/00* (2006.01)
*C09C 1/22* (2006.01)
*B05D 5/06* (2006.01)

(52) U.S. Cl. ....... 106/439; 106/31.9; 106/415; 106/418; 106/456; 106/457; 106/459; 106/482; 106/489; 427/218; 427/219; 428/403; 428/404; 428/406; 524/439

(58) Field of Classification Search ................... 106/415, 106/418, 439, 31.9, 456, 457, 459, 482, 489; 524/218, 439; 427/219; 428/403, 404, 406
See application file for complete search history.

(56) References Cited

U.S. PATENT DOCUMENTS

| | | | |
|---|---|---|---|
| 3,926,659 A | 12/1975 | Bernhard et al. | |
| 4,146,403 A * | 3/1979 | Armanini et al. | 106/418 |
| 6,719,838 B2 | 4/2004 | Heider et al. | |
| 7,850,775 B2 * | 12/2010 | Hollman et al. | 106/418 |
| 2003/0097965 A1 | 5/2003 | Heider et al. | |
| 2008/0279796 A1 * | 11/2008 | Handrosch et al. | 424/63 |
| 2009/0185992 A1 * | 7/2009 | Conan et al. | 424/61 |

FOREIGN PATENT DOCUMENTS

| | | |
|---|---|---|
| DE | 2313331 A1 | 9/1974 |
| EP | 1306412 A | 5/2003 |
| WO | PCTEP2007010869 R | 2/2009 |

* cited by examiner

*Primary Examiner* — Anthony Green
(74) *Attorney, Agent, or Firm* — Millen, White, Zelano & Branigan, P.C.

(57) ABSTRACT

The present invention relates to pearlescent pigments based on flake-form substrates which have at least one FeOOH layer and at least one $TiO_2$ layer or at least one $TiO_2/SiO_2/TiO_2$ layer package, and to the use thereof, inter alia, in paints, coatings, printing inks, powder coatings, plastics and in particular in care and decorative cosmetics.

20 Claims, No Drawings

PEARLESCENT PIGMENTS

The present invention relates to pearlescent pigments based on flake-form substrates which have at least one FeOOH layer and at least one $TiO_2$ layer or $TiO_2/SiO_2/TiO_2$ layer package, and to the use thereof in paints, coatings, printing inks, powder coatings and in particular in care and decorative cosmetics.

Pearlescent pigments having iron oxide coatings are known in the prior art. In general, mica flakes are coated with $Fe_2O_3$ or $Fe_2TiO_5$. However, cracks frequently occur in iron oxide coatings on mica, which reduce the colour brightness.

The object of the present invention is to provide pearlescent pigments having iron oxide coatings which do not have disadvantages of this type.

Surprisingly, it has now been found that flake-form substrates which have both an FeOOH layer and also a $TiO_2$ layer or $TiO_2/SiO_2/TiO_2$ layer package combine a novel combination of bright interference colour and bright, pure mass tone. Due to the lower calcination temperatures, the formation of pseudobrookite at the interfaces between Ti- and Fe-containing layers is additionally prevented.

The invention therefore relates to pearlescent pigments which are distinguished by the fact that they have (A) at least one FeOOH layer
and
(B) at least one $TiO_2$ layer or at least one $TiO_2/SiO_2/TiO_2$ layer package
and
(C) optionally an outer colourless coating comprising one or more layers having a refractive index of <1.8.

In the pearlescent pigments according to the invention, it is possible to combine any $TiO_2$ interference colour with any FeOOH mass tone, which results in interesting colour variants; it is possible here to deposit both a layer sequence (A)(B) and also the layer sequence (B)(A) on the substrate, i.e. a $TiO_2$+FeOOH,
FeOOH+$TiO_2$,
$TiO_2$+$SiO_2$+$TiO_2$+FeOOH or
FeOOH+$TiO_2$+$SiO_2$+$TiO_2$ layer sequence is located on the substrate Since the pearlescent pigments according to the invention have a very smooth surface, they are particularly suitable, owing to their very good skin feel, for care and decorative cosmetics. Furthermore, they are suitable for pigmenting paints, coatings, powder coatings, printing inks, plastics, for colouring seed, for finishing, colouring or coating food and pharmaceutical products, including medicament coatings, and for the preparation of pigment compositions and dry preparations.

Owing to the achievable combinations of interference colour and mass tone in the beige and skin-coloured colour region, the pearlescent pigments according to the invention are very attractive, in particular, for topical applications.

Suitable base substrates for the pearlescent pigments according to the invention are on the one hand opaque and on the other hand transparent flake-form substrates. Particular preference is given to transparent flake-form substrates.

Suitable substrates are, in particular, natural and synthetic mica, talc, kaolin, flake-form iron or aluminium oxides, glass flakes, $SiO_2$ flakes, $TiO_2$ flakes, graphite flakes, synthetic support-free flakes, liquid crystal polymers (LCPs), holographic pigments, BiOCl flakes, metal flakes, optionally passivated such as, for example, aluminium flakes, flakes made from aluminium bronzes, brass bronzes, zinc bronzes, titanium bronzes or other comparable materials.

Of the said substrates, particular preference is given to glass flakes, furthermore natural mica flakes and synthetic mica flakes, for example comprising fluorophlogophite. Very particularly preferred substrates are glass flakes coated with an $SiO_2$ layer.

The size of the base substrates is not crucial per se and can be matched to the particular application. In general, the flake-form substrates have an average thickness of <10 µm, in particular an average thickness of 0.15-5 µm. The size in the two other dimensions is on average usually 1-1000 µm, preferably 2-250 µm, in particular 5-150 µm.

If the substrate is a glass flake, it preferably comprises silicate glasses, such as soda-lime glass, borosilicate glass, aluminosilicate glass, lead crystal glass, window glass, E, A, C or ECR glass or Duran glass.

The glass flakes preferably have an average thickness of <10 µm, in particular on average 50 nm-5 µm, particularly preferably 50-800 nm and very particularly preferably 50-600 nm.

The glass flakes are furthermore preferably distinguished by a refractive index of 1.2-2.1, preferably 1.3-1.9 and very particularly preferably 1.4-1.6.

Suitable substrate flakes preferably have an aspect ratio (ratio:diameter/thickness) of 5-750, in particular 10-300, very particularly preferably 20-200.

The thickness of the individual layers (A), (B) and (C) is essential for the optical properties of the pigment. In order to obtain a particularly intense interference colour in a pigment, it is necessary, inter alia, for the thickness of the individual layers to be matched precisely to one another. Irrespective of the type and refractive index of the individual layers, the thickness of each layer is generally 1-1000 nm, in particular 10-800 nm and particularly preferably 20-600 nm.

The FeOOH layer (A) preferably has on average layer thicknesses of 10-550 nm, in particular 15-400 nm and very particularly preferably 20-350 nm. The FeOOH layer generally makes up 0.01-300% by weight, in particular 1-200% by weight and very particularly preferably 2-100% by weight, based on the substrate.

If layer (B) is a $TiO_2$ layer, this can be either in the anatase form or in the rutile form. It is preferably a rutile layer. The $TiO_2$ layer preferably has on average layer thicknesses of 5-550 nm, in particular 10-400 nm and very particularly preferably 15-350 nm. Numerous methods are known from the literature for the rutilisation of $TiO_2$. The host used for the epitactic growth of $TiO_2$ in the rutile modification is preferably $SnO_2$, i.e. a thin $SnO_2$ layer, which usually has layer thicknesses of 1-50 nm, in particular 1-40 nm and very particularly preferably 1-30 nm, is generally applied before the coating with $TiO_2$.

If layer (B) is a $TiO_2/SiO_2/TiO_2$ layer package, the layer thicknesses of the $TiO_2$ layers may be identical or different. The product can contain one $TiO_2/SiO_2/TiO_2$ layer package or alternatively a plurality thereof one on top of the other. However, the sum of all layers precipitated onto the substrate should not exceed a total thickness of 3 µm. The individual $TiO_2$ layers in the package may each be in the anatase or rutile modification. They are preferably in the form of a rutile layer. The individual $TiO_2$ layer in the layer package preferably has layer thicknesses of 5-550 nm, in particular 10-400 nm, very particularly preferably 15-350 nm. The $SiO_2$ layer in the layer package preferably has layer thicknesses of 1-1000 nm, in particular 10-800 nm and very particularly preferably 20-600 nm. The total layer thickness of the $TiO_2/SiO_2/TiO_2$ layer package is accordingly preferably <2.100 nm, in particular <1.600 nm and very particularly preferably <1.300 nm.

Materials which are suitable for layer (C) are colourless, low-refractive-index materials, preferably metal oxides or the corresponding oxide hydrates. Examples which may be mentioned are: $SiO_2$, $Al_2O_3$, $AlO(OH)$, $B_2O_3$, $MgF_2$, $MgSiO_3$ or a mixture of the said compounds. The thickness of layer (C) is preferably on average 1-1.000 nm, in particular 10-800 nm and very particularly preferably 20-600 nm. This layer may occur once or more than once in the layer sequence. However, it may also be completely absent.

It is frequently advisable to introduce an $SiO_2$ interlayer between the substrate and the first layer on the substrate and/or after the FeOOH layer if at least one further layer follows. This interlayer (Z) preferably has layer thicknesses of 1-1.000 nm, in particular 1-500 nm and very particularly preferably 1-300 nm.

In the case of glass as substrate, the $SiO_2$ layer protects the substrate surface against chemical modification, such as swelling, bleaching-out of glass constituents or dissolution in aggressive acidic coating solutions. Irrespective of the type of substrate, however, the adhesion of the coating(s) following the $SiO_2$ layer very generally also increases. In this way, the overall stability of the coating and thus of the pigment is increased. Furthermore, the $SiO_2$ interlayer has a positive effect on the luster of the pigment.

Particularly preferred pearlescent pigments have the following layer sequences:
substrate+$SiO_2$+$TiO_2$+FeOOH
substrate+$SiO_2$+$TiO_2$+$SiO_2$+FeOOH
substrate+$SiO_2$+FeOOH+$TiO_2$
substrate+$SiO_2$+$TiO_2$+$SiO_2$+$TiO_2$+FeOOH
substrate+$SiO_2$+$TiO_2$+$SiO_2$+$TiO_2$+$SiO_2$+FeOOH
substrate+$SiO_2$+FeOOH+$SiO_2$+$TiO_2$
substrate+$SiO_2$+FeOOH+$SiO_2$+$TiO_2$+$SiO_2$+$TiO_2$
substrate+$SiO_2$+FeOOH+$TiO_2$+$SiO_2$+$TiO_2$
substrate+$TiO_2$+FeOOH
substrate+$TiO_2$+$SiO_2$+FeOOH
substrate+FeOOH+$TiO_2$
substrate+$TiO_2$+$SiO_2$+$TiO_2$+FeOOH
substrate+$TiO_2$+$SiO_2$+$TiO_2$+$SiO_2$+FeOOH
substrate+FeOOH+$SiO_2$+$TiO_2$
substrate+FeOOH+$SiO_2$+$TiO_2$+$SiO_2$+$TiO_2$
substrate+FeOOH+$TiO_2$+$SiO_2$+$TiO_2$ The pearlescent pigments according to the invention can be prepared relatively easily. The layers are preferably applied by wet-chemical methods, it being possible to use the wet-chemical coating methods developed for the preparation of pearlescent pigments. Methods of this type are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 355, DE 32 11 602, DE 32 35 017 or also in further patent documents and other publications known to the person skilled in the art.

In the case of wet coating, the substrate particles are suspended in water, and one or more hydrolysable metal salts are added at a pH which is suitable for hydrolysis and is selected so that the metal oxides or metal oxide hydrates are precipitated directly onto the flakes without significant secondary precipitations occurring. The pH is usually kept constant by simultaneous metered addition of a base and/or acid. The pigments are subsequently separated off, washed and dried at 50-180° C.

The coating can furthermore also be carried out in a fluidised-bed reactor by gas-phase coating, it being possible to use correspondingly, for example, the methods proposed in EP 0045 851 A1 and EP 0 106 235 A1 for the preparation of pearlescent pigments.

If the said pearlescent pigments have a $TiO_2$ layer, this can be in the rutile or anatase modification. It is preferably in the rutile modification. Rutilisation is known to the person skilled in the art and can be carried out, for example, as described in U.S. Pat. No. 4,038,099, U.S. Pat. No. 5,433,779, U.S. Pat. No. 6,626,989, WO 03/097749, U.S. Pat. No. 4,086,100, U.S. Pat. No. 4,867,794. Particular preference is given to rutilisation using tin oxide, as described, for example, in U.S. Pat. No. 4,867,794.

The pearlescent pigments according to the invention can also additionally be provided with a protective layer in order to increase the light, weather and chemical stability or in order to increase the compatibility in various media. Depending on the type of aftercoating, this can optionally be applied still in the reaction suspension of the base pigment directly after precipitation of the final pigment layer is complete. In the case of some aftercoatings, by contrast, it is advisable to re-suspend the ready-calcined pearlescent pigment in a suitable medium and only then to carry out the aftercoating. Suitable aftercoatings or aftertreatments are, for example, the methods described in German Patent 22 15 191, DE-A 31 51 354, DE-A 32 35 017 or DE-A 33 34 598. This aftercoating further increases the chemical stability or simplifies handling of the pigment, in particular incorporation into various media. In order to improve the wettability, dispersibility and/or compatibility with the application media, functional coatings of $Al_2O_3$ or $ZrO_2$ or mixtures or mixed phases thereof can be applied to the pigment surface. Furthermore, organic or combined organic/inorganic aftercoatings are possible, for example with silanes, as described, for example, in EP 0090259, EP 0 634 459, WO 99/57204, WO 96/32446, WO 99/57204, U.S. Pat. No. 5,759,255, U.S. Pat. No. 5,571,851, WO 01/92425 or in J. J. Ponjeé, Philips Technical Review, Vol. 44, No. 3, 81 ff. and P. H. Harding J. C. Berg, J. Adhesion Sci. Technol. Vol. 11 No. 4, pp. 471-493.

The pearlescent pigments according to the invention are compatible with a multiplicity of colour systems, preferably from the area of paints, coatings, printing inks and cosmetic formulations. For the preparation of printing inks, for example for gravure printing, flexographic printing, offset printing, offset overprint varnishing, a multiplicity of binders, in particular water-soluble types, is suitable, as marketed, for example, by BASF, Marabu, Pröll, Sericol, Hartmann, Gebr. Schmidt, Sicpa, Aarberg, Siegberg, GSB-Wahl, Follmann, Ruco or Coates Screen INKS GmbH. The printing inks can be water-based or solvent-based. The pearlescent pigments are furthermore also suitable for applications in the agricultural sector, for example for greenhouse sheeting, for colouring seed, and, for example, for colouring tarpaulins.

Since the pearlescent pigments according to the invention combine a particularly clear colour with intense interference colours and high brightness, particularly effective effects can be achieved therewith in the various application media, for example in cosmetic formulations, such as nail varnishes, lipsticks, compact powders, gels, lotions, emulsions, soaps and toothpastes.

It goes without saying that, for the various applications, the pearlescent pigments according to the invention can also advantageously be used in a blend with organic dyes, organic pigments or other pigments, such as, for example, transparent and opaque white, coloured and black pigments, and with flake-form iron oxides, organic pigments, holographic pigments, LCPs (liquid crystal polymers) and conventional transparent, coloured and black luster pigments based on metal oxide-coated mica and $SiO_2$ flakes, etc. The pigments according to the invention can be mixed in any ratio with commercially available pigments and fillers.

Fillers which may be mentioned are, for example, natural and synthetic mica, glass beads or glass powders, nylon powders, pure or filled melamine resins, talc, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances.

There are no restrictions regarding the particle shape of the filler. In accordance with requirements, it can be, for example, flake-form, spherical, needle-shaped, crystalline or amorphous.

The pigments according to the invention can of course also be combined in the formulations with raw materials and assistants of any type. These include, inter alia, oils, fats, waxes, film formers, preservatives and assistants which generally determine the applicational properties, such as, for example, thickeners and rheological additives, such as, for example, bentonites, hectorites, silicon dioxides, Ca silicates, gelatines, high-molecular-weight carbohydrates and/or surface-active assistants, etc.

The pigments according to the invention can furthermore also be combined with cosmetic active compounds. Suitable active compounds are, for example, insect repellents, inorganic UV filters, such as, for example, $TiO_2$, UV A/BC protection filters (for example OMC, B3, MBC), including in encapsulated form, antiageing active compounds, vitamins and derivatives thereof (for example vitamin A, C, E, etc.), self-tanning agents (for example DHA, erythrulose, inter alia) and further cosmetic active compounds, such as, for example, bisabolol, LPO, VTA, ectoin, emblica, allantoin, bioflavonoids and derivatives thereof.

Organic UV filters are generally incorporated into cosmetic formulations in an amount of 0.5 to 10 percent by weight, preferably 1-8%, and inorganic filters in an amount of 0.1 to 30%.

In self-tanning creams, lotions, sprays, etc., comprising, for example, the self-tanning agent DHA (dihydroxyacetone) and an effect pigment having a final $TiO_2$ or iron oxide layer, for example a glass flake coated with $TiO_2$ (anatase), the DHA is slowly degraded in the formulation. On use of the pearlescent pigments according to the invention in the formulation, the action of the DHA is fully retained or the degradation is at least significantly slowed if an aftercoating, in particular a final layer of $SiO_2$, has been applied.

The compositions according to the invention may, in addition, comprise further conventional skin-protecting or skin-care active compounds. These may in principle be all active compounds known to the person skilled in the art.

Particularly preferred active compounds are pyrimidinecarboxylic acids and/or aryl oximes.

Of the cosmetic applications, particular mention may be made of the use of ectoin and ectoin derivatives for the care of aged, dry or irritated skin. Thus, EP-A-0 671 161 describes, in particular, that ectoin and hydroxy-ectoin are employed in cosmetic compositions, such as powders, soaps, surfactant-containing cleansing products, lipsticks, rouge, make-up, care creams and sunscreen preparations.

Application forms of the cosmetic formulations which may be mentioned are, for example: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower preparations. Any desired customary vehicles, assistants and, if desired, further active compounds may be added to the composition.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as, for example, fatty acid esters, fatty alcohols, silicone oils, natural oils, such as vegetable oils and oily plant extracts, paraffin oils, lanolin oils, or mixtures of these substances.

The cosmetic compositions may exist in various forms. Thus, they can be, for example, a solution, a water-free composition, an emulsion or micro-emulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Further embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

Solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The concentration of the pearlescent pigment according to the invention in the application system to be pigmented is generally between 0.01 and 70% by weight, preferably between 0.1 and 50% by weight and in particular between 1.0 and 10% by weight, based on the total solids content of the system. It is generally dependent on the specific application and can be up to 100% in the case of loose powders. The use concentration of the pigment mixture according to the invention extends from 0.01% by weight in shampoo to 70% by weight in compact powder.

No limits are set for the concentrations of the pigment mixtures according to the invention in the formulation. They can be—depending on the application—between 0.001 (rinse-off products, for example shower gels) and 100% (for example luster-effect articles for particular applications).

The use concentration of the pearlescent pigment with organic and inorganic coloured pigments and dyes, of natural or synthetic origin, such as, for example, chromium oxide, ultramarine, spherical $SiO_2$ or $TiO_2$ pigments, is dependent on the application medium and the effect to be achieved.

The formulations comprising the pigment mixtures according to the invention can belong to the lipophilic, hydrophilic or hydrophobic type. In heterogeneous formulations having discrete aqueous and non-aqueous phases, the pigment mixtures according to the invention may in each case be present in only one of the two phases or alternatively distributed over both phases.

The pH values of the formulations can be between 1 and 14, preferably between 2 and 11 and particularly preferably between 5 and 8.

Pharmaceutical and food products are coloured and/or finished by adding the pearlescent pigment according to the invention, alone or in combination with colorants, such as, for example, natural or nature-identical dyes, to the product to be coloured in the desired mixing ratios, preferably in amounts of 0.005 to 30% by weight, in particular 0.001 to 20% by weight.

The admixing of natural or nature-identical dyes, organic or inorganic coloured pigments or colouring natural fruit and plant extracts approved for the foods sector enables the colour effect in the product to be influenced and at the same time enables novel colour effects to be achieved.

Suitable natural or nature-identical dyes are, in particular, E 101, E 104, E 110, E 124, E 131, E 132, E 140, E 141, E 151, E 160a. Furthermore, it is also possible to admix coloured pigments with the pearlescent pigment according to the invention, such as, for example, E 171, E 172, E 153.

The proportion of colorants besides the pearlescent pigment, based on the food or pharmaceutical product, is preferably in the range from 0.5 to 25% by weight. The dye employed can likewise be fruit and plant extracts, such as, for example, carrot juice, beetroot juice, elderberry juice, hibiscus juice, paprika extract or aronia extract.

The total concentration of all pigments in the product to be pigmented should not exceed 50% by weight, based on the product. It is generally dependent on the specific application.

Various active-compound additives, such as, for example, vitamins, enzymes, trace elements, proteins, carbohydrates, essential fats and/or minerals, can also be added to the food and pharmaceutical products, where the total amount of active compounds, based on the food or pharmaceutical product, should not exceed 25% by weight. The amount of active compounds or active-compound mixtures is preferably 0.01-20% by weight, based on the product.

The products are coloured by adding the pearlescent pigment, alone or in combination with further colorants, to the product to be coloured, directly or in the presence of water and/or an organic solvent, in the desired mixing ratios, simultaneously or successively, during or after production thereof, before or after shaping (for example during extrusion, pelleting, expansion, granulation, etc.). Admixing of the pearlescent pigments according to the invention with pulverulent or loose powders is likewise possible.

On incorporation into the product matrix itself, the use amount of the pearlescent pigments according to the invention is preferably 0.005-15% by weight, in particular 1-10% by weight. In the case of surface colouring of food and pharmaceutical products, the use concentration of the pigments according to the invention is preferably <10% by weight.

Products which are suitable for colouring or coating are, for example, sugar products, cake decorations, pressed products, dragees, chewing gums, gum products, fondant products, marzipan products, filling compositions, cocoa and fat glazes, chocolate and chocolate-containing products, ice cream, cereals, snack products, coating compositions, cake glazes, scattered sugar decorations, nonpareils, jelly and gelatine products, sweets, liquorice, icing, candyfloss, fat, sugar and cream compositions, blancmange, desserts, flan glaze, cold fruit soups, soft drinks and carbonated beverages, beverages with stabilising additives, such as, for example, carboxymethylcellulose, acidified and unacidified milk products, such as, for example, quark, yoghurt, cheese, cheese rinds, sausage casings, etc.

In the case of coated food and pharmaceutical products, it is possible to combine the pearlescent pigments according to the invention with aroma substances (powder or liquid aromas), acids and/or with sweeteners, such as, for example, aspartame, in order additionally to reinforce the visual effect in terms of flavour.

The invention thus relates to all formulations from the foods and pharmaceutical sector comprising the pearlescent pigments according to the invention, alone or in combination with further colorants, such as, for example, natural and/or nature-identical dyes, fruit and plant extracts, coloured pigments, and/or with one or more active compounds, such as, for example, vitamins, enzymes, trace elements, proteins, carbohydrates, essential fats.

The invention thus also relates to the use of the pearlescent pigments in formulations such as paints, coatings, automobile paints, powder coatings, printing inks, security printing inks, plastics, ceramic materials, glasses, paper, in paper coating, in toners for electrophotographic printing processes, for colouring seed, in greenhouse sheeting and tarpaulins, as absorbers in the laser marking of paper and polymers, such as, for example, plastics, for coating and/or colouring food and pharmaceutical products, in cosmetic formulations, for the preparation of pigment pastes with water, organic and/or aqueous solvents, for the preparation of pigment compositions and dry preparations, such as, for example, granules, chips, briquettes or pellets.

The following examples are intended to explain the invention in greater detail, but without restricting it.

EXAMPLES

Example 1

200 g of mica flakes (natural potassium mica) of the 10-60 μm fraction are made up to a concentration of 100 g/l using deionised water. The suspension is warmed to 80° C. The pH is subsequently adjusted to 1.8 using hydrochloric acid (15% of HCl). At constant pH, about 30 ml of a TiOCl$_2$ solution (400 g/l) are metered in and at the same time counter-titrated with 32% w/w NaOH. When the addition is complete, the mixture is stirred for a further 10 min. A pH of 4.0 is subsequently set using NaOH. An FeOOH layer is then precipitated on to give a gold-green colour by metered addition of an FeCl$_3$ solution (14.25% of Fe) at constant pH, and the mixture is stirred for a further 30 min.

The pigment having a pale-green interference colour and a gold-ochre mass tone is cooled to room temperature and filtered off, washed until salt-free and dried at 110° C.

Example 2

200 g of synthetic mica flakes of the 10-60 µm fraction are made up to a concentration of 100 g/l using deionised water. The suspension is warmed to 80° C. About 430 g of an FeCl$_3$ solution (14.25% of Fe) are metered in with vigorous stirring. During this addition, the pH is kept constant at 4.0 using sodium hydroxide solution (32% of NaOH). The pH is subsequently lowered to 1.8 using hydrochloric acid (15% of HCl), and about 30 ml of a TiOCl$_2$ solution (400 g/l of TiCl$_4$) are metered in at this pH. During this addition, the pH is kept constant using sodium hydroxide solution (32% of NaOH).

In order to precipitate the subsequent SiO$_2$ layer, firstly the pH is adjusted to 7.5 using sodium hydroxide solution (32% of NaOH). About 400 g of a water-glass solution (13% of SiO$_2$) are then metered in.

When the addition is complete, the pH is lowered to 2.0 using hydrochloric acid (15% of HCl), and a solution of 3 g of SnCl$_4$×5 H$_2$O in 10 ml of hydrochloric acid (37% of HCl) and 90 ml of deionised water are metered in at this pH. During this addition, the pH is again kept constant by countertitration with sodium hydroxide solution (32% of NaOH).

For the following TiO$_2$ layer, the pH of the reaction suspension is firstly lowered to 1.8 using hydrochloric acid (15% of HCl), and 476 ml of TiCl$_4$ solution (400 g/l) are metered in at this pH. During this addition, the pH is kept constant using sodium hydroxide solution (32% of NaOH). The mixture is stirred for a further 15 min. After cooling to room temperature, the resultant product is filtered off, washed until salt-free and dried at 110° C. A blue-violet interference colour and an ochre-yellow mass tone are evident.

Example 3

200 g of glass flakes having an average thickness of 850 nm and of the 10-100 µm fraction are made up to a concentration of 100 g/l using deionised water. The suspension is warmed to 75° C. with stirring. A pH of 9 is set using sodium hydroxide solution (32% of NaOH). 112 g of a sodium water-glass solution (26.8% of SiO$_2$) are subsequently metered in. During this addition, the pH is kept constant at 9 by countertitration with hydrochloric acid (18% of HCl). When the addition is complete, the mixture is stirred for a further 30 min. A pH=1.8 is subsequently set using hydrochloric acid (18% of HCl), and the mixture is stirred for a further 15 min. At constant pH=1.8, an SnCl$_4$ solution (3 g of SnCl$_4$×5H$_2$O in 15 ml of conc. HCl (25%)/85 ml of deionised water) is metered in, during which the mixture is countertitrated with sodium hydroxide solution (32% of NaOH). A TiCl$_4$ solution (400 g of TiCl$_4$/l) is then metered in. During this addition, the pH is kept constant by countertitration with sodium hydroxide solution (32% of NaOH). The addition is carried out until a red interference colour is achieved. The precipitation process here is monitored in accordance with the hue (hue angle arc tan b*/a*)° by means of in-line control via COPRA measurement of the suspension.

A pH of 3.0 is subsequently set using sodium hydroxide solution (32% of NaOH). By metered addition of an FeCl$_3$ solution (14.25% of Fe), an FeOOH layer is subsequently precipitated to a pale-green interference colour at constant pH, and the mixture is stirred for a further 30 min. Finally, the pH is adjusted to 6 using NaOH.

After cooling to room temperature, the pigment having a gold-green interference colour and a gold-ochre mass tone is filtered off, washed until salt-free and dried at 110° C.

Use Examples

Example A1

Shower Gel

| Phase | Raw material | INCI | % |
|---|---|---|---|
| A | Ronastar ® Golden Sparks (1) | CALCIUM ALUMINUM BOROSILICATE, SILICA, CI 77891 TITANIUM DIOXIDE), TIN OXIDE | 0.05 |
| | Pigment according to Example 3 | | 0.20 |
| | Keltrol CG-SFT (2) | XANTHAN GUM | 1.10 |
| | Water, demineralised | WATER, AQUA (WATER) | 54.80 |
| B | Plantacare 2000UP (3) | DECYL GLUCOSIDE | 20.00 |
| | Texapon ASV 50 (3) | SODIUM LAURETH SULFATE, SODIUM LAURETH-8 SODIUM LAURETH SULFATE, SODIUM LAURETH-8 MAGNESIUM LAURETH-8 SULFATE, SODIUM OLETH SULFATE, MAGNESIUM OLETH SULFATE | 3.60 |
| | Bronidox L (3) | PROPYLENE GLYCOL, 5-BROMO-5-NITRO-1,3-DIOXANE | 0.30 |
| | Frag 280851 Fruit Cocktail (4) | PARFUM | 0.20 |
| | 0.1% of Sicovit Quinoline Yellow 70 E 104 in water (5) | AQUA (WATER), WATER, CI 47005 (ACID YELLO ACID YELLOW 3W 3), | 8.30 |
| | 0.1% of Dragocolor True Blue in water (6) | AQUA (WATER), WATER, CI 42090 (FD&C BLUE NO. 1), FD&C BLUE NO. 1 | 1.30 |
| C | Citric acid monohydrate (1) | CITRIC ACID | 0.15 |
| | Water, demineralised | WATER, AQUA (WATER) | 10.00 |

Preparation:

Phase A: Introduce the water into the reactor and stir in the pigment. Slowly scatter in the Keltrol CG-SFT with stirring and stir until it has completely dissolved (do not homogenise). Add the constituents of phase B individually to phase A. Dissolve the citric acid monohydrate in water and add to the batch and stir slowly until everything is homogeneously distributed. Adjust the pH to 6.0-6.5 with addition of citric acid (if required).

Sources of supply:
(1) Merck KGaA/Rona ®
(2) C. P. Kelco
(3) Cognis GmbH
(4) Drom
(5) BASF AG
(6) Symrise

Example A2

Eye Shadow

| Phase | Raw material | INCI | % |
|---|---|---|---|
| A | Xirona ® Magic Mauve (1) | SILICA, CI 77891 (TITANIUM DIOXIDE), TIN OXIDE | 27.00 |
|  | Microna ® Matte Blue (1) | CI 77510 (FERRIC FERROCYANIDE), MICA | 3.00 |
|  | Talc (1) | TALC | 34.50 |
|  | Pigment according to Example 2 |  | 15.00 |
|  | Potato starch (2) | POTATO STARCH, SOLANUM TUBEROSUM (POTATO STARCH) | 7.50 |
|  | Magnesium stearate (1) | MAGNESIUM STEARATE | 2.50 |
| B | Isopropyl stearate (3) | ISOPROPYL STEARATE | 9.14 |
|  | Cetyl palmitate (1) | CETYL PALMITATE | 0.53 |
|  | Ewalin 1751 (4) | PETROLATUM | 0.53 |
|  | Perfume oil Elegance + 79228 D MF (5) | PARFUM | 0.20 |
|  | Propyl 4-hydroxy-benzoate (1) | PROPYLPARABEN | 0.10 |

Preparation:
Combine and pre-mix the constituents of phase A. Subsequently add the molten phase B dropwise to the powder mixture with stirring. The powders are transferred into powder pans of large diameter and pressed at 80 bar.
Sources of supply:
(1) Merck KGaA/Rona ®
(2) Suedstaerke GmbH
(3) Cognis GmbH
(4) H. Erhard Wagner GmbH
(5) Symrise

Example A3

Creamy Eye Shadow

| Phase | Raw material | INCI | % |
|---|---|---|---|
| A | Xirona ® Golden Sky (1) | SILICA, CI 77891 (TITANIUM DIOXIDE), TIN OXIDE | 14.00 |
|  | Pigment according to Example 2 |  | 6.00 |
|  | Unipure Green LC 789 CF (2) | CI 77289 (CHROMIUM HYDROXIDE GREEN) | 3.00 |
| B | Crodamol PMP (3) | PPG-2 MYRISTYL ETHER PROPIONATE | 41.58 |
|  | Syncrowax HGLC (3) | C18-36 ACID TRIGLYCERIDE | 11.00 |
|  | Syncrowax HRC (3) | TRIBEHENIN | 3.30 |
|  | Miglyol 812 N (4) | CAPRYLIC/CAPRIC TRIGLYCERIDE | 15.40 |
|  | Stearic acid (1) | STEARIC ACID | 3.30 |
|  | Antaron V-216 (5) | PVP/HEXADECENE CO-POLYMER | 2.20 |
|  | Oxynex ® K liquid (1) | PVP/HEXADECENE CO-POLYMER, ASCORBIC ACID, CITRIC ACID | 0.11 |
|  | Propyl 4-hydroxybenzoate (1) | PROPYLPARABEN | 0.11 |

Preparation:
Heat phase B to about 80° C. until everything has melted and cool to 65° C. The pearlescent pigment and the ground chromium oxide of phase A are then added with stirring. The eye shadow is packaged at 65° C.
Sources of supply:
(1) Merck KGaA/Rona ®
(2) Les Colorants Wackherr
(3) Croda GmbH
(4) Sasol Germany GmbH
(5) ISP Global Technologies

Example A4

Shampoo

| Phase | Raw material | INCI | % |
|---|---|---|---|
| A | Pigment according to Example 1 |  | 3.00 |
|  | Carbopol ETD 2020 (2) | ACRYLATES/C10-30 ALKYL ACRYLATE CROSSPOLYMER | 0.90 |
|  | Water, demineralised | AQUA (WATER) | 60.60 |
| B | Triethanolamine extra pure (1) | TRIETHANOLAMINE | 0.90 |
|  | Water, demineralised | AQUA (WATER) | 10.00 |
| C | Plantacare 2000 UP (3) | DECYL GLUCOSIDE | 20.00 |
|  | Texapon ASV 50 (3) | SODIUM LAURETH SULFATE, SODIUM LAURETH-8, SULFATE, MAGNESIUM LAURETH SULFATE, SULFATE, MAGNESIUM LAURETH SULFATE, SULFATE, MAGNESIUM OLETH SULFATE | 4.35 |
|  | Bronidox L (3) | PROPYLENE GLYCOL, 5-BROMO-5-NITRO-1,3-DI-OXANE | 0.20 |
|  | Perfume oil 200 524 (4) | PARFUM | 0.05 |
|  | Dye solution (q.s.) |  | 0.00 |

Preparation:
For phase A, stir the filler into the water. Acidify using a few drops of citric acid (10%) in order to reduce the viscosity and slowly scatter in the Carbopol with stirring. When completely dissolved, slowly add phase B. The constituents of phase C are then added successively. Adjust the pH to 6.0-6.5.
Sources of supply:
(1) Merck KGaA/Rona ®
(2) Noveon
(3) Cognis GmbH
(4) Fragrance Resources

Example A5

Nail Varnish

| Phase | Raw material | INCI | % |
|---|---|---|---|
| A | Xirona ® Le Rouge (1) | SILICA, CI 77491 (IRON OXIDES), | 1.75 |
|  | Pigment according to Example 3 |  | 1.00 |
|  | Ronastar ® Red Sparks (1) | CALCIUM ALUMINUM BOROSILICATE, CI 77891 CALCIUM ALUMINUM BOROSILICATE, CI 77891 | 0.25 |
|  | Colouring base ref. 690 (2) | BUTYL ACETATE, ETHYL ACETATE, NITROCELLULOSE, PHTHALIC, ANHYDRIDE/ TRIMELLITIC ANHYDRIDE/ GLYCOLS COPOLYMER, CI 15850 (D&C RED NO. 7 CALCIUM LAKE), D&C RED NO. 7 CALCIUM LAKE, ISOPROPYL ALCOHOL, ACETYL TRIBUTYL CITRATE, STEARALKONIUM HECTORITE | 2.00 |
|  | Thixotropic nail varnish base 155 (2) | BUTYL ACETATE, ETHYL ACETATE, NITROCELLULOSE, ACETYL TRIBUTYL CITRATE, | 95.00 |

-continued

| Phase | Raw material | INCI | % |
|---|---|---|---|
| | | PHTHALIC ANHYDRIDE/ TRIMELLITIC ANHYDRIDE/ GLYCOLS COPOLYMER, ISOPROPYL ALCOHOL, STEARALKONIUM HECTORITE, ADIPIC ACID/FUMARIC ACID/PHTHALIC ACID/TRICYCLODECANE DIMETHANOL COPOLYMER, CITRIC ACID | |

Preparation:
The pigments are weighed out together with the varnish base, mixed well by hand using a spatula and subsequently stirred at 1000 rpm for 10 min.
Sources of supply:
(1) Merck KGaA/Rona ®
(2) Durlin/Bergerac NC

The invention claimed is:

1. Pearlescent pigments based on a flake-form substrate, which have the following layer sequence:
   substrate+$SiO_2$+$TiO_2$+FeOOH,
   substrate+$SiO_2$+$TiO_2$+$SiO_2$+FeOOH,
   substrate+$SiO_2$+FeOOH+$TiO_2$,
   substrate+$SiO_2$+$TiO_2$+$SiO_2$+$TiO_2$+FeOOH,
   substrate+$SiO_2$+$TiO_2$+$SiO_2$+$TiO_2$+$SiO_2$+FeOOH,
   substrate+$SiO_2$+FeOOH+$SiO_2$+$TiO_2$,
   substrate+$SiO_2$+FeOOH+$SiO_2$+$TiO_2$+$SiO_2$+$TiO_2$,
   substrate+$SiO_2$+FeOOH+$TiO_2$+$SiO_2$+$TiO_2$,
   substrate+$TiO_2$+$SiO_2$+FeOOH,
   substrate+$TiO_2$+$SiO_2$+$TiO_2$+FeOOH,
   substrate+$TiO_2$+$SiO_2$+$TiO_2$+$SiO_2$+FeOOH,
   substrate+FeOOH+$SiO_2$+$TiO_2$,
   substrate+FeOOH+$SiO_2$+$TiO_2$+$SiO_2$+$TiO_2$, or
   substrate+FeOOH+$TiO_2$+$SiO_2$+$TiO_2$,
and optionally a colourless coating comprising one or more layers having a refractive index of <1.8.

2. Pearlescent pigments according to claim 1, wherein the substrate is selected from the group consisting of natural mica, synthetic mica, BiOCl flakes, glass flakes, $Fe_2O_3$ flakes, graphite flakes, $Al_2O_3$ flakes, $SiO_2$ flakes and $TiO_2$ flakes.

3. Pearlescent pigments according to claim 1, wherein the substrate is glass flakes comprising silicate glass, soda-lime glass, borosilicate glass, aluminosilicate glass, lead crystal glass, window glass, A, C, E, or ECR glass.

4. Pearlescent pigments according to claim 1, wherein the substrate has an average thickness of <10 μm.

5. Pearlescent pigments according to claim 1, wherein the substrate has, on average, a particle diameter of 1-1000 μm.

6. Pearlescent pigments according to claim 1, wherein the pigments have an aspect ratio of 5-750.

7. Pearlescent pigments according to claim 1, wherein the FeOOH layer has, on average, layer thicknesses of 10-550 nm.

8. Pearlescent pigments according to claim 1, wherein the $TiO_2$ layer has, on average, layer thicknesses of 5-550 nm.

9. Pearlescent pigments according to claim 1, wherein the $TiO_2$/$SiO_2$/$TiO_2$ layer sequence has a total layer thickness of <2100 nm.

10. Pearlescent pigments according to claim 1, which contain a colourless coating comprising one or more layers having a refractive index of <1.8, which have, on average, a layer thickness of 1-1000 nm.

11. Pearlescent pigments according to claim 1, which have the following layer sequence:
   substrate+$SiO_2$+$TiO_2$+FeOOH,
   substrate+$SiO_2$+$TiO_2$+$SiO_2$+FeOOH,
   substrate+$SiO_2$+FeOOH+$TiO_2$,
   substrate+$SiO_2$+$TiO_2$+$SiO_2$+$TiO_2$+FeOOH,
   substrate+$SiO_2$+$TiO_2$+$SiO_2$+$TiO_2$+$SiO_2$+FeOOH,
   substrate+$SiO_2$+FeOOH+$SiO_2$+$TiO_2$,
   substrate+$SiO_2$+FeOOH+$SiO_2$+$TiO_2$+$SiO_2$+$TiO_2$, or
   substrate+$SiO_2$+FeOOH+$TiO_2$+$SiO_2$+$TiO_2$.

12. Pearlescent pigments according to claim 1, wherein the $TiO_2$ layer is in the rutile modification.

13. Pearlescent pigments according to claim 1, which have the following layer sequence:
   substrate+$TiO_2$+$SiO_2$+FeOOH,
   substrate+$TiO_2$+$SiO_2$+$TiO_2$+FeOOH, or
   substrate+$TiO_2$+$SiO_2$+$TiO_2$+$SiO_2$+FeOOH.

14. Pearlescent pigments according to claim 1, which have the following layer sequence:
   substrate+FeOOH+$SiO_2$+$TiO_2$,
   substrate+FeOOH+$SiO_2$+$TiO_2$+$SiO_2$+$TiO_2$, or
   substrate+FeOOH+$TiO_2$+$SiO_2$+$TiO_2$.

15. Pearlescent pigments according to claim 1, which have the following layer sequence:
   substrate+$SiO_2$+$TiO_2$+$SiO_2$+$TiO_2$+FeOOH,
   substrate+$SiO_2$+$TiO_2$+$SiO_2$+$TiO_2$+$SiO_2$+FeOOH,
   substrate+$SiO_2$+FeOOH+$SiO_2$+$TiO_2$+$SiO_2$+$TiO_2$,
   substrate+$SiO_2$+FeOOH+$TiO_2$+$SiO_2$+$TiO_2$,
   substrate+$TiO_2$+$SiO_2$+$TiO_2$+FeOOH,
   substrate+$TiO_2$+$SiO_2$+$TiO_2$+$SiO_2$+FeOOH,
   substrate+FeOOH+$SiO_2$+$TiO_2$+$SiO_2$+$TiO_2$, or
   substrate+FeOOH+$TiO_2$+$SiO_2$+$TiO_2$.

16. Pearlescent pigments according to claim 1, which have the following layer sequence:
   substrate+$SiO_2$+$TiI_2$+FeOOH,
   substrate+$SiO_2$+$TiO_2$+$SiO_2$+FeOOH,
   substrate+$SiO_2$+FeOOH+$TiO_2$,
   substrate+$SiO_2$+FeOOH+$SiO_2$+$TiO_2$,
   substrate+$TiO_2$+$SiO_2$+FeOOH, or
   substrate+FeOOH+$SiO_2$+$TiO_2$.

17. Pearlescent pigments according to claim 1, wherein the substrate has, on average, a particle diameter of 5-150 μm.

18. A process for preparing pearlescent pigments according to claim 1, comprising coating the flake-form substrates by a wet-chemical method or by a CVD or PVD process.

19. A product selected from the group consisting of paints, coatings, powder coatings, printing inks, plastics, seed coloring, food coating, pharmaceutical product coating, food coloring, pharmaceutical product coloring, absorbers in the laser marking of paper, absorbers in the laser marking of polymers, care cosmetics product, decorative cosmetics product, pigment compositions and dry preparations, comprising pearlescent pigments according to claim 1 and a carrier.

20. Dry preparations in the form of granules, chips, briquettes, pellets comprising pearlescent pigments according to claim 1 and a carrier.

* * * * *

UNITED STATES PATENT AND TRADEMARK OFFICE
CERTIFICATE OF CORRECTION

| | |
|---|---|
| PATENT NO. | : 8,114,211 B2 |
| APPLICATION NO. | : 12/520151 |
| DATED | : February 14, 2012 |
| INVENTOR(S) | : Carsten Handrosch et al. |

It is certified that error appears in the above-identified patent and that said Letters Patent is hereby corrected as shown below:

Column 14, line 39 (Claim 16), reads: "substrate+$SiO_2$+$TiI_2$+FeOOH,"
It should read -- substrate+$SiO_2$+$TiO_2$+FeOOH, --.

Signed and Sealed this
Twenty-second Day of May, 2012

David J. Kappos
*Director of the United States Patent and Trademark Office*